United States Patent
Paradis

[11] Patent Number: 6,063,062
[45] Date of Patent: May 16, 2000

[54] UNIVERSAL LUER ACTIVATABLE AND SWABBABLE ANTIREFLUX VALVE

[76] Inventor: Joseph R. Paradis, P.O. Box 22238, Hilton Head Island, S.C. 29926

[21] Appl. No.: 08/840,468

[22] Filed: Apr. 18, 1997

[51] Int. Cl.⁷ .................................................... A61M 5/00
[52] U.S. Cl. ...................... 604/249; 604/256; 251/149.1
[58] Field of Search .................. 251/149.1, 149.6; 604/30, 33, 246, 247, 249, 256, 283

[56] References Cited

U.S. PATENT DOCUMENTS

| | | | |
|---|---|---|---|
| 4,473,369 | 9/1984 | Lueders et al. | 604/244 |
| 4,745,950 | 5/1988 | Mathieu | 137/798 |
| 5,269,771 | 12/1993 | Thomas et al. | 604/213 |
| 5,441,487 | 8/1995 | Vedder | 604/167 |
| 5,492,147 | 2/1996 | Challender et al. | 137/614.05 |
| 5,520,666 | 5/1996 | Choudhury et al. | 604/283 |
| 5,578,059 | 11/1996 | Patzer et al. | 604/249 |

*Primary Examiner*—Wynn Wood Coggins
*Assistant Examiner*—Deborah Blyveis
*Attorney, Agent, or Firm*—George E. Kersey, Esq.

[57] ABSTRACT

Apparatus formed by a housing having an inlet and an inwardly biased and circumferentially open flexible seal depending from the inlet to engage and seal a fitting as it enters the inlet. A stationary probe within the housing extends axially from an outlet to the inlet, with the probe having a passageway thereinto connected to the outlet and the input is sealed when there is a reflux of fluid into the outlet.

19 Claims, 12 Drawing Sheets

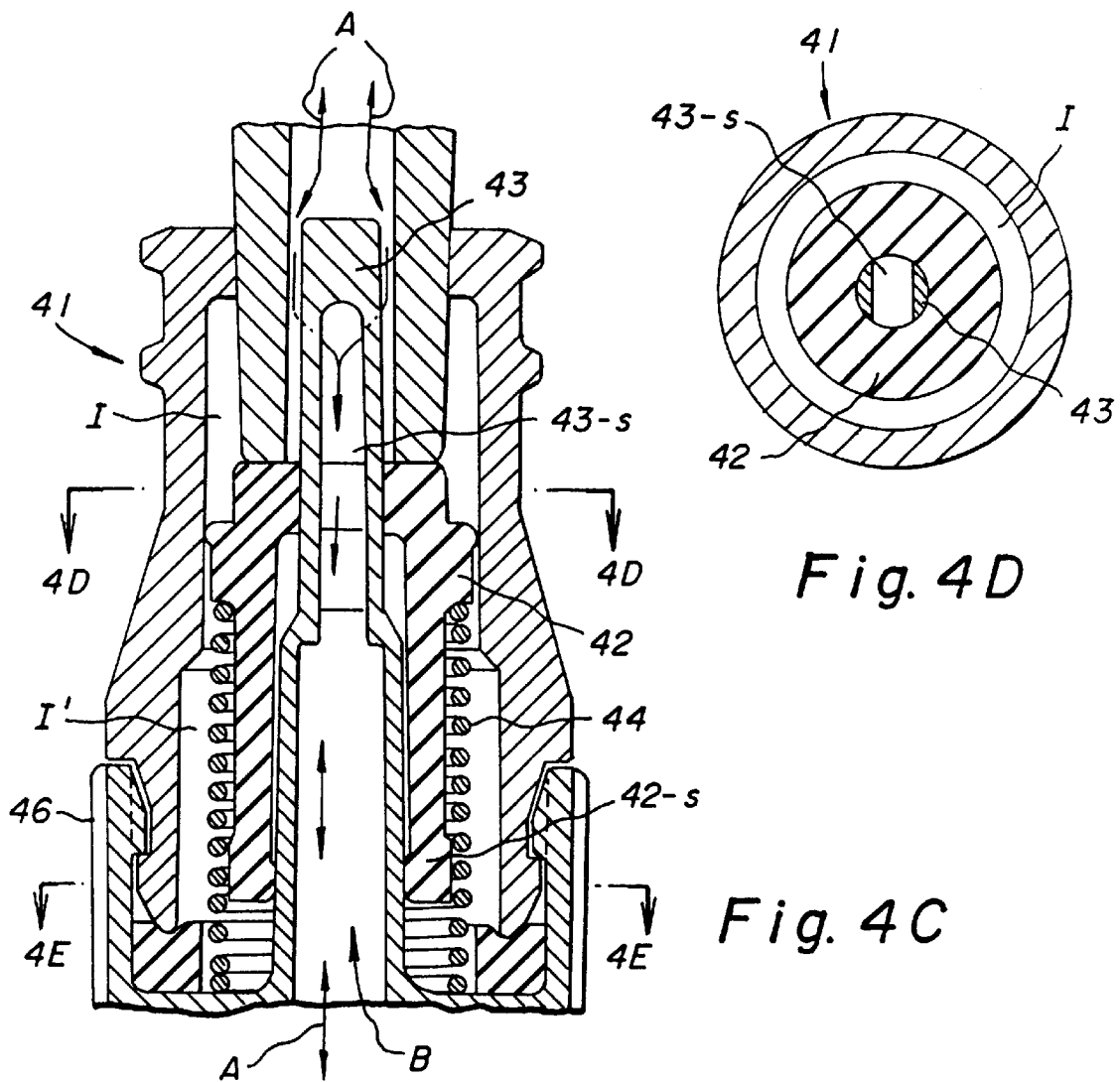
Fig. 4C
Fig. 4D
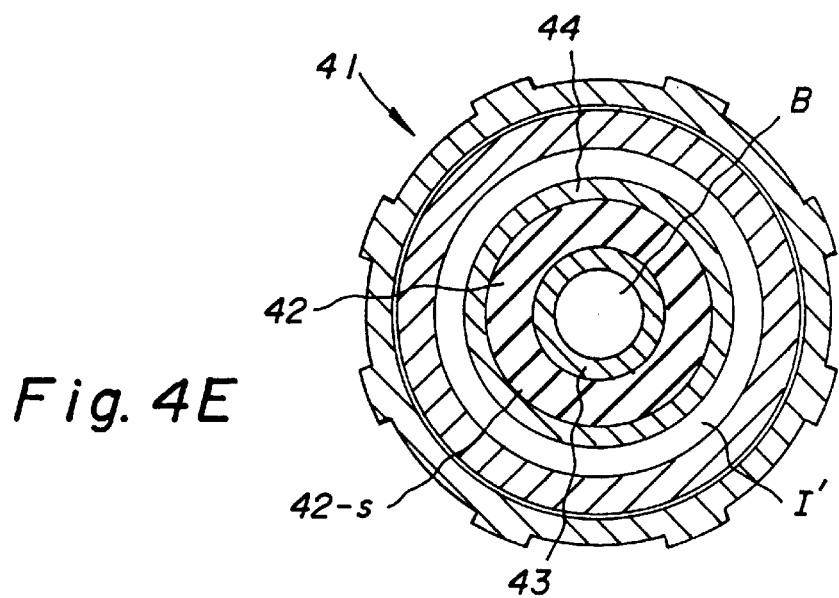
Fig. 4E

UNIVERSAL LUER ACTIVATABLE AND SWABBABLE ANTIREFLUX VALVE

BACKGROUND OF THE INVENTION

This invention relates to flow control and, more particularly, to Luer activatable and swabbable valves for the needleless control of fluids.

A valve is a device that controls flow, for example, in two directions. Where fluids need to be introduced into, or removed from, the body, it is common practice to do so through a flow control valve connected to a catheter, which is a slender hollow tube inserted into a body passage or cavity for passing fluids. A catheter permits the control of fluid flow both into and out of the body passage.

For example, medication can be injected into a flow control valve connected to a catheter. In prior practice, medication from the syringe has been introduced using a needle, but this can be undesirable, since in modern medical practice, needle sticks are to be avoided. A number of attempts have been made to achieve the introduction of medication or the extraction of fluid without the need for using syringes with needles.

Illustrative examples of attempted needleless control of fluids are disclosed in Newgard et al., U.S. Pat. No. 5,064,416; Sivert, U.S. Pat. No. 4,915,687; Jackson, U.S. Pat. No. 4,429,856; Kilmarx, U.S. Pat. No. 3,352,531 and Faust et al. U.S. Pat. No. 5,116,021.

All of these illustrative arrangements have the objection that air borne and other pathogens can enter their inlets without being easily sterilized. While attempts have been made to maintain sterility by capping the inlets, the requirement of caps presents open passages during connection and additional complexity and expense. In addition, caps can become dislodged during storage and handling, rending the devices unusable or requiring special sterilization procedures.

Newgard '416 is typical in having a long inlet passage before there is access to a moveable member which is pierceable and controls flow by the extent to which a valving member can be dilated. Sivert, Johnson, Kilmarx and Faust are similarly objectionable.

Moreover, where valves are accessible by Luer fittings, instead of needles, the Luer fitting enters a long inlet passage before making contact with a moveable member that is unseated to permit fluid flow. Because of tolerance considerations, the inlet passage must be wide enough to accommodate the largest diameter Luer fitting. This means that for smaller diameter Luer fittings, within the tolerance specifications, there is a variable gap between the inlet wall of the valve and the Luer fitting being used to access the valve.

The result is a substantially large area for contamination by pathogens that cannot be neutralized by swabbing of the valve.

Accordingly, it is an object of the invention to overcome the problem of pathogen contamination that arises because of the need for valve inlets to accommodate a wide variety of Luer fitting diameters within the tolerance specifications that apply to such fittings.

Still another consideration is desire to operate flow control devices with low "cracking" pressures, i.e. the pressure at which a control member moves away from its seat. For such devices, it is desirable to use relatively thin diaphragms. Unfortunately, thin diaphragms pose problems of stability. The diaphragm may move slightly away from its central position and become lodged against a side wall, causing a problem of leakage.

The catheters used with flow control valves are of various types. One type includes a tubular member for the introduction of fluids into a blood channel which may be venous or arterial. Another type is a double-walled flexible tube which terminates at its outer end in two separate branches. One branch continues as an outer tube and terminates at its inner end in a inflatable portion.

The other branch continues as an inner tube with a through passage that extends to the inflatable portion of the outer tube. There are various other types of catheters as well.

With all types of catheters, it is desirable to be able to control the through flow of fluid using a suitable valve, which can be used in non-catheter applications as well.

Accordingly, it is another object of the invention to provide a miniature flow control valve which can be used without needles and is swabbable by being easily wiped with disinfectant across its inlet to eliminate contamination and pathogens. A related object is to allow the valve to be readily usable with devices, such as catheters, to control fluid flow while restricting operation by a patient or unauthorized personnel.

A further object of the invention is to provide a simple and expendable valve, which can be mass produced, readily assembled and provide ease of operation.

SUMMARY OF THE INVENTION

In accomplishing the foregoing and related objects, the miniature flow control valve of the invention is provided with "universal" Luer adaptation by having, depending from its inlet, a flexible seal that engages and seals the Luer fitting as it enters the inlet, regardless of size, for Luer fittings with the standard range of tolerances for such fittings. The flexible seal functions regardless of the Luer fitting diameter, and thus eliminates the possibility of pathogen contamination from the presence of any gap between the fitting and the interior of the valve before activation.

The invention also provides a tubular housing having centered at its inlet bore a solid-ended and non-moveable probe surrounded by an annular seal plug so that both the probe and the seal plug can be cleansed by swabbing, i.e., wiping, the inlet end before the annular seal plug is depressed by, for example, the blunt end of a syringe in order to engage an internal passageway of the probe and permit passage of fluid from the syringe through the valve.

The seal plug acts against both the inlet flexible seal and the central probe. The plug abuts an inwardly facing shoulder or valve seat of the flexible seal, and is held in its closed position by, for example, a spring, which can be elastomeric, until the seal plug is disengaged from the valve seat by an external member, such as the hollow blunt end of a syringe containing fluid that is to be injected through the valve, for example, into a catheter.

In accordance with a broad aspect of the invention, the housing has an input and output; a probe within the housing extends from the output flush with the input or beyond it; the probe has a passageway thereinto connected to the output; and a depressible member seals the input, surrounding the probe and being depressible therealong to expose the passageway.

Because of the extension of the probe beyond the input, swabbing of the probe and the seal plug is permitted before the depression of the sealing member.

The housing input has an entrance and the sealing means can be substantially flush with the entrance. Where the entrance has a prescribed level, the sealing member can terminate at the prescribed level, or below it.

The probe is configured to facilitate location with an external member, such as a Luer fitting prior to depressing the sealing member. The probe can terminate in a rounded end beyond the input or in a flattened end.

The seal plug seals the housing and the probe at the housing input, and the seal plug can seal the probe at a plurality of positions therealong. The seal plug can include provision for applying a vertical force thereto for positive sealing of the valve upon removal of any external valve opening member, such as a Luer fitting.

In a method of the invention the steps include: sealing an input by a pre-loaded force on a depressible seal plug surrounding a solid-ended probe extending beyond the input; and depressing the seal plug to uncover, in the probe, a passageway connected to an output. As a result, the depression of the seal plug permits flow from the input to the output.

The method of the invention departs from prior art methods which employ slotted seal members and require internal spikes that are sharp or blunt and are needed to penetrate the slotted seal member, requiring heavy opening forces that result in cutting of the seal member because of the need for seal member expansion within a restricted body volume. After several activations with such devices, the result is the introduction of undesirable contaminant particles in the fluid flow.

The seal plug of the invention is depressible from a position substantially flush with the entrance to the input. Where the entrance has a prescribed level, the seal plug is depressible from the prescribed level, or from below the prescribed level.

The method further includes the step of locating the probe by an outside member, such as a male Luer termination, for depressing the circular seal plug. The step of locating the probe in the center bore of the male Luer termination takes place at the rounded end of the probe beyond the input, or astride a flattened end beyond the input.

The sealing to the probe can be at a plurality of different locations therealong, spring force can be applied to return the seal plug to a seal position at the input, and during this return of the seal plug, a wiping action of the seal plug occurs along the input bore of the housing and along the outside diameter of the probe.

In a method of manufacturing a swabbable valve the steps include: (a) providing a housing having an input and containing a probe within the housing extending from a output to beyond the input; (b) providing in the probe, a passageway that is connected to the output; and (c) sealing the input by a member surrounding the probe, engaging the housing, and depressible in a wiping action therealong to expose the passageway. The extension of the probe beyond the input permits the swabbing thereof before the depression of the seal plug.

A miniature valve in accordance with the invention includes a tubular housing having an outlet and an inlet at a level surrounded by an exterior surface; a bore extending from the exterior surface into the housing; a stationary probe centered at the inlet at the level of the exterior surface, with the probe having an internal channel extending to the outlet, and a passageway at a position where there is communication outwardly from the interior channel; and there is an annular seal plug between the probe and the interior of the housing for sealing the inlet, with the annular seal plug being depressible to the position of the passageway in the stationary probe. Because of the location of the probe and the annular seal plug relative to the inlet easy swabbing across the inlet and exterior surface is facilitated. Swabbing is further facilitated where the annular seal plug is flush with the inlet.

The apparatus of the invention encompasses means having an exterior surface at a level containing an inlet; means centered in the inlet at the level of the exterior surface and having a passageway for communicating with the inlet and extending to an interior channel for communicating with an outlet; and means depressible at the inlet to the position of the passageway; whereby the exterior surface, the depressible member and the channel containing member can be swabbed to reduce contamination and pathogens before the depressible member is depressed. Moreover, the flexible input seal of the invention allows the accommodation of a wide range of Luer fitments, regardless of tolerance variations within the applicable manufacturing limits, to prevent the entrance of pathogens and other contaminants into the fluid stream once activation has taken place.

The housing of the invention has an interior with a bore extending from an inlet into the housing; a stationary probe is centered in the housing and included in any hypothetical extension of the inlet surface; the probe has exterior and an interior channel extending to the outlet, with a passageway communicating between the interior channel and the exterior of the probe; and an annular member between the probe and the interior of the housing seals the inlet and is depressible to the position of the passageway in the probe.

In accordance with still another aspect, the invention provides a housing having an input and an output; a probe within the housing extending axially from the output to the input; with the probe having a passageway thereinto connected to the output; and means sealing the input, surrounding the probe when there is a reflux of fluid into the output. The sealing means can be a flexible circular seal having an axially extending wall, which engages the probe.

The sealing means can include a member surrounding the probe and the axially extending wall can engage the member by being included in a housing that surrounds the member below the input. The member can include a channel that permits flow from the output to the axially extending wall, with the channel extending transversely in relation to the axially extending wall, which can take the form of frustum of a hollow cone.

An actuator can depress the sealing member and pressure applied through the actuator can open a passageway to the outlet.

In a method of limiting reflux flow in a valve formed by a housing having an input and an output, the steps can include providing a probe within the housing extending axially from the output to the input; including in the probe a passageway thereinto connected to the output; and sealing the input in relation to the probe when there is a reflux of fluid into the output.

The method can further include the step of sealing the input by a flexible circular seal having an axially extending wall, and the seal plug can be engaged by the axially extending wall. The probe can be surrounded by the seal plug engaged by the axially extending wall.

The axially extending wall can be included in a housing surrounding the seal plug at the input inlet. Flow is permitted from the output to the axially extending wall. A channel can be provided that extends transversely in relation to the axially extending wall to permit the flow.

The method can further include the step of axially extending the wall to form the frustum of a hollow cone, and an actuator can be applied to depress the sealing member and cause pressure applied through the actuator to open a passageway to the outlet.

The method also can include the steps of sealing an input by a depressible member surrounding a probe extending to the input; and depressing the member along the probe in sealing engagement therewith. Pressure can be applied at the input to unseal the engagement of the member with the probe.

DESCRIPTION OF THE DRAWINGS

Other aspects of the invention will become apparent after considering several illustrative embodiments taken in conjunction with the drawings in which:

FIG. 4C is a expanded sectional view of the valve and Luer actuator end of FIG. 4A showing the depression of the Luer end into the bore of the swabbable check valve;

FIG. 4D is a sectional view of FIG. 4C, taken along the lines 4D—4D, illustrating a portion of the flow channel;

FIG. 4E is a sectional view of FIG. 4C, taken along the lines 4E—4E, illustrating the further aspects of sealing;

DETAILED DESCRIPTION

Figure 1A:
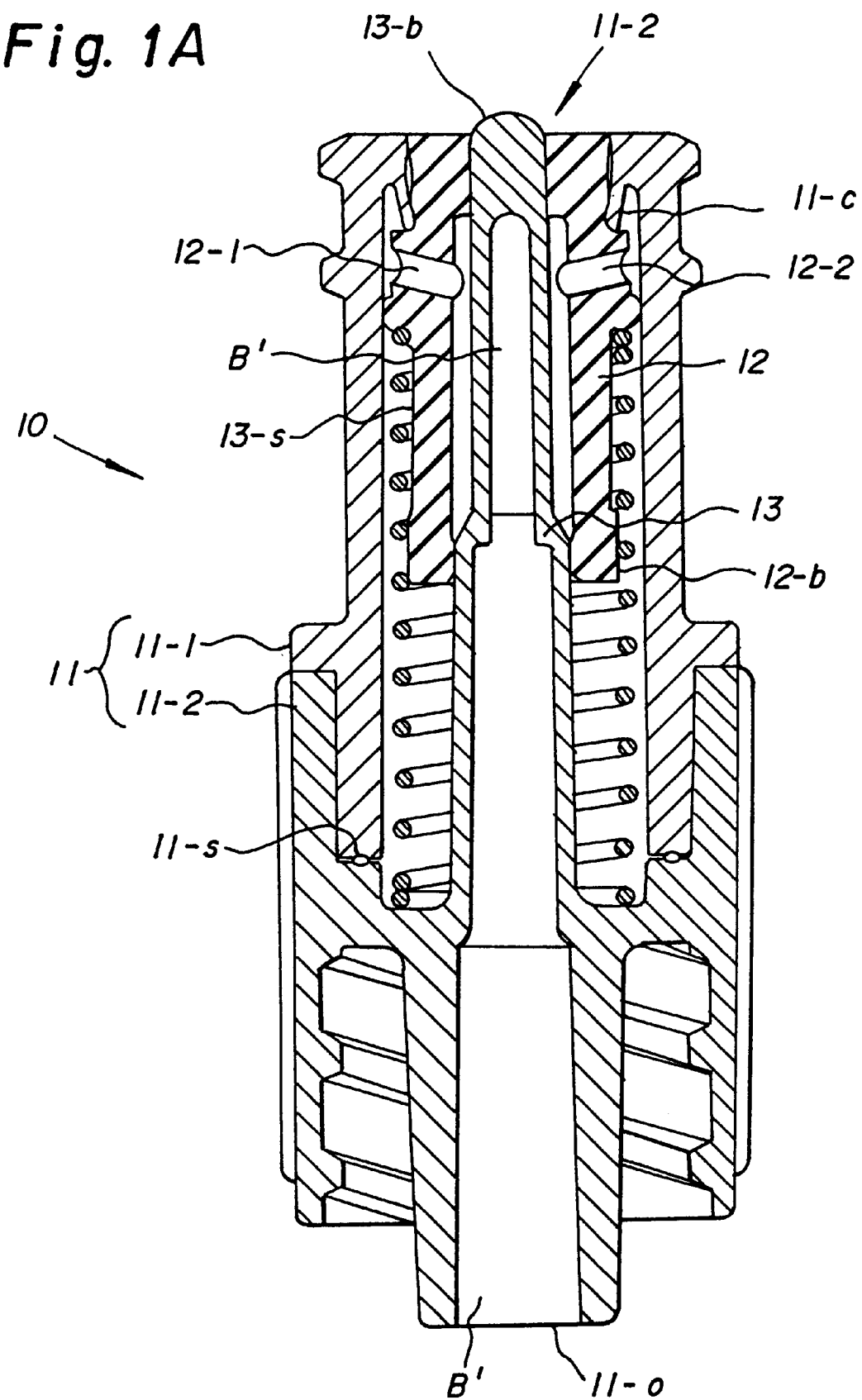
FIG. 1A is a sectional view of an alternative embodiment of the invention.

With reference to the drawings, an embodiment of the invention is provided by the check valve 10 of FIG. 1A, which includes a tubular housing 11 with two parts 11-1 and 11-2 joined together by an ultrasonic seal 11-s. The part 11-1, which occupies an "upper" position in FIG. 1A, contains an annular seal plug 12 that surrounds the upper portion of a stationary probe 13. The probe 13 is centered in the bore B' of the housing 11 and contains an axial slot 13-s that extends to the bore B' of the housing 11.

The upper portion of the seal plug 12, below the inlet 11-i of the housing 11-1, slidably engages the upper end of the probe 13, while the intermediate portion of the sealing member 12, adjoining the slot 13-s, is spaced from the probe 13, and the probe is in further sealing engagement with the member 12 at its base 12-b.

In addition, the upper portion of the seal plug 12 is in contact with the part 11-1 and extends downwardly into contact with a circular flexible seal 11-c that allows the valve 10 to accommodate a wide variety of male Luer fitments and syringes since the circular flexible seal 11-c is biased inwardly towards the bore B' and expands outwardly depending upon the diameter of the fitment or syringe that is inserted into the inlet 11-i.

The circular flexible seal 11-c also serves the further function of limiting reflux when the valve 11 is included with a catheter that is being inserted into a patient. During such insertion and entry of the catheter needle into a vessel, such as a vein, blood pressure exerted through the valve can cause the upward flow of blood into and through the valve in an action that is known as "reflux", defined generally as "a flowing back". The flexible circular seal 11-c of the invention guards against back pressure through the valve 11 by operating in conjunction with the lateral apertures 12-1 and 12-2 in the sealing member 12. Accordingly, when there is a flow of fluid into the valve 11 through the outlet 11-o, the apertures 12-1 and 12-2 channel the reverse flow against the circular seal 11-c and prevent reflux of the fluid beyond the inlet 11-i.

Figure 1B:
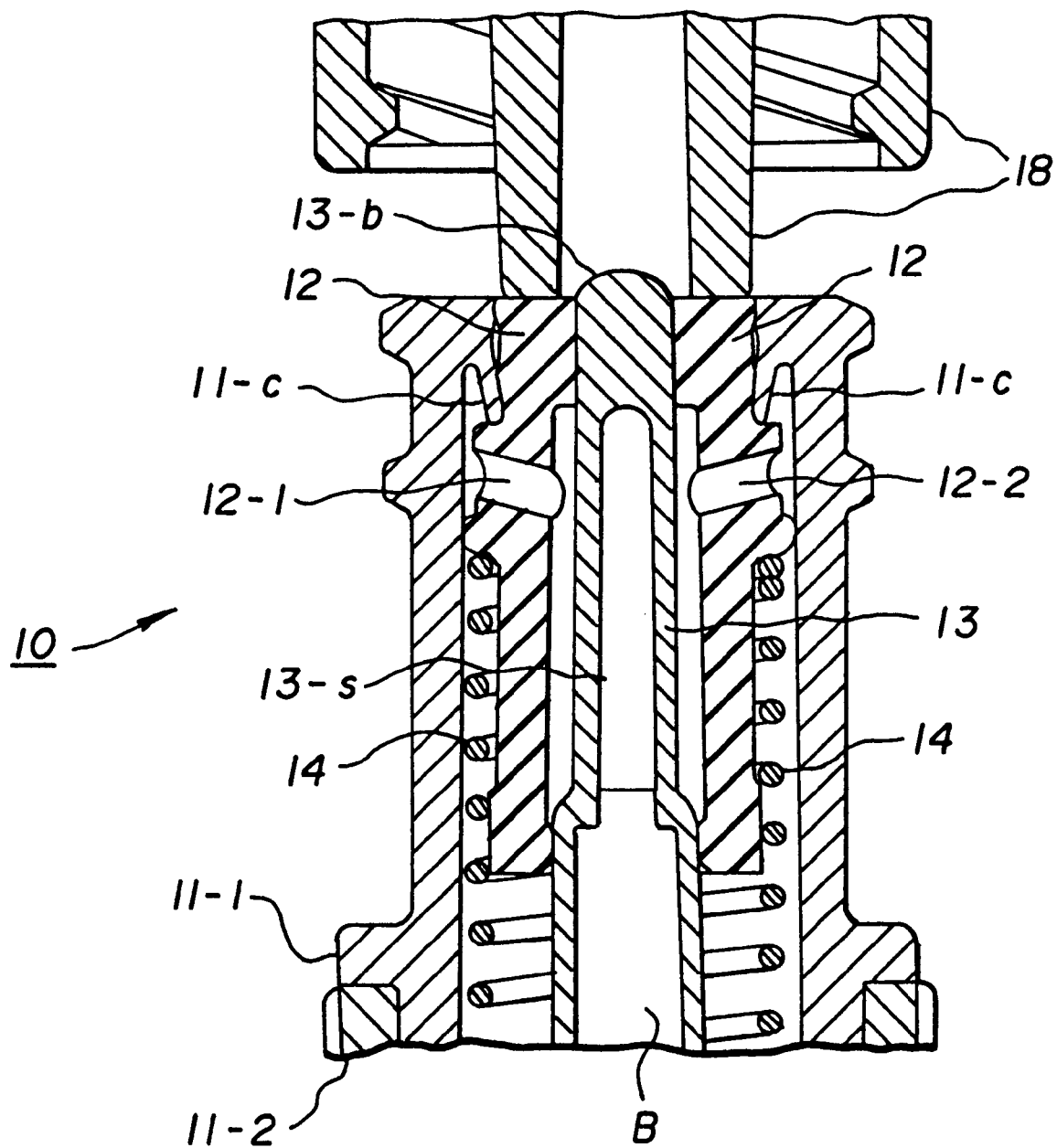
FIG. 1B is a partial sectional view of FIG. 1A showing the valve in contact with an actuator taking the form of a Luer tip.

A closed and blunt end 13-b of the probe 13 is elevated above the valve inlet 11-i to serve as a locator for an external member by which the sealing member 12 is depressible, as shown in FIG. 1B where a Luer male outlet 18 has been brought into contact with the sealing member 12, after being guided in position by the locator tip 13-b of the probe 13.

The sealing member 12 is held in its operative sealing position against the circular seal 11-c by a helical spring 14, but other spring structures may be employed as well as described previously. Accordingly, while the sealing member 12, desirably elastomeric, is shown as being of a length shorter than the axial dimension of the housing 11, it may be elongated and incorporated functionally replacing the spring 14.

The probe 13 is fixedly held, preferably by being integral with, and extending upwardly from the lower part 11-2. Like the tubular housing 11, the probe 13 can be formed of a moldable plastic.

Since the valve 10 is operated by an external member such as the Luer end of a syringe, the tip 13-b of FIG. 1A which has been reproduced in FIG. 1B, serves as a fitment locator, of which FIG. 1B is merely representative.

When the valve 10 is to be operated, an external member such as the male Luer outlet 18 of FIG. 1B is brought into contact with the sealing member 12, after being guided in position by the locator tip 13-b of the probe 13.

Figure 1C:
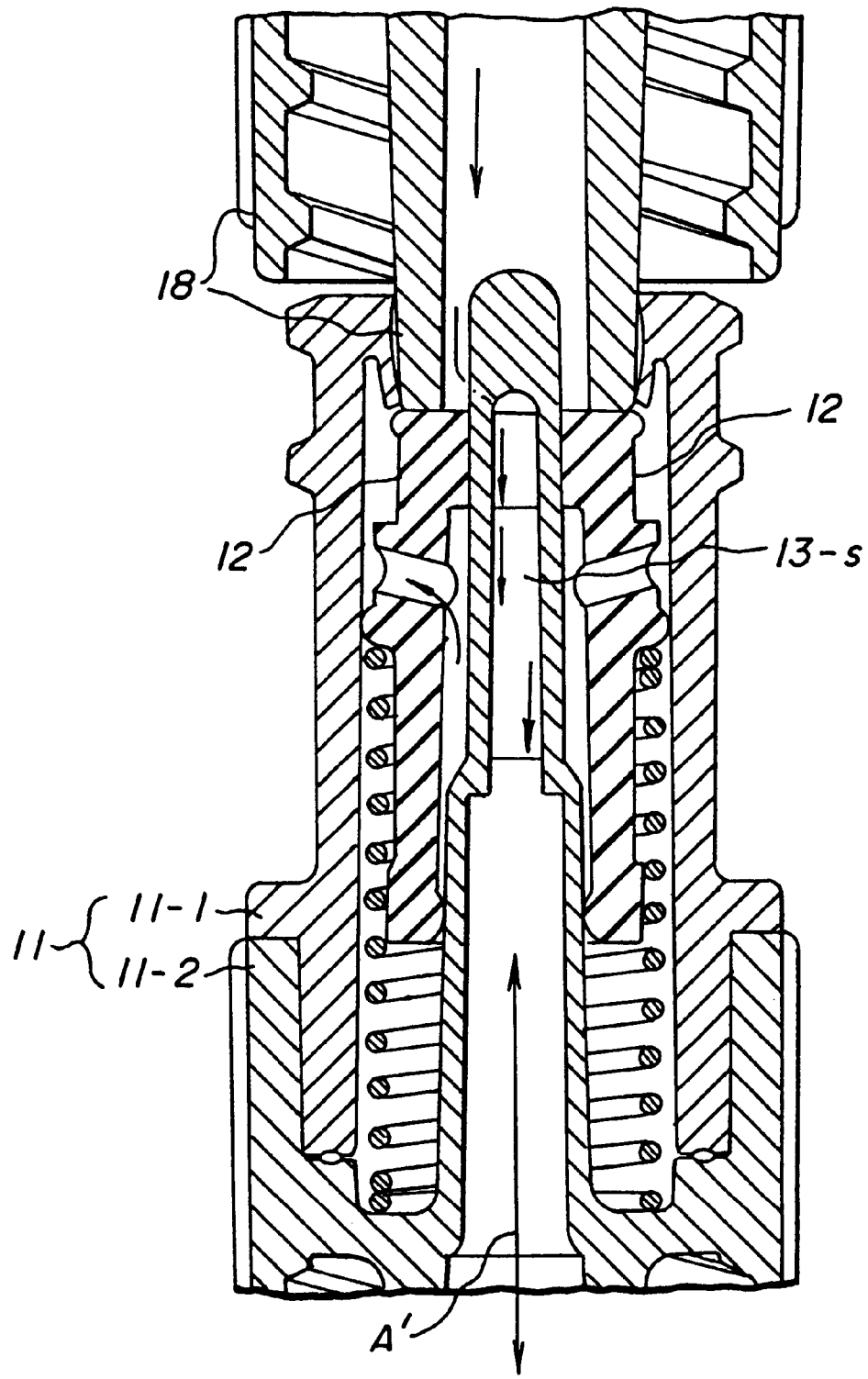
FIG. 1C is a further sectional view showing the Luer tip of FIG. 1B initially depressing the seal plug of the check valve of 1B.

The sealing member 12 may be pushed or forced inwardly from its normal seating position. When forced inwardly as shown in FIG. 1C, the top of the sealing member 12 extends below the transverse slot 13-s and thus establishes open communication for fluid through the central bore of the housing 11 in either direction, e.g. inwardly or outwardly of the valve 10, as indicated by the double-headed arrows A'. To open a wider channel, the the actuator 18 depresses the sealing member 12 still further as shown in FIG. 1D.

Figure 1D:
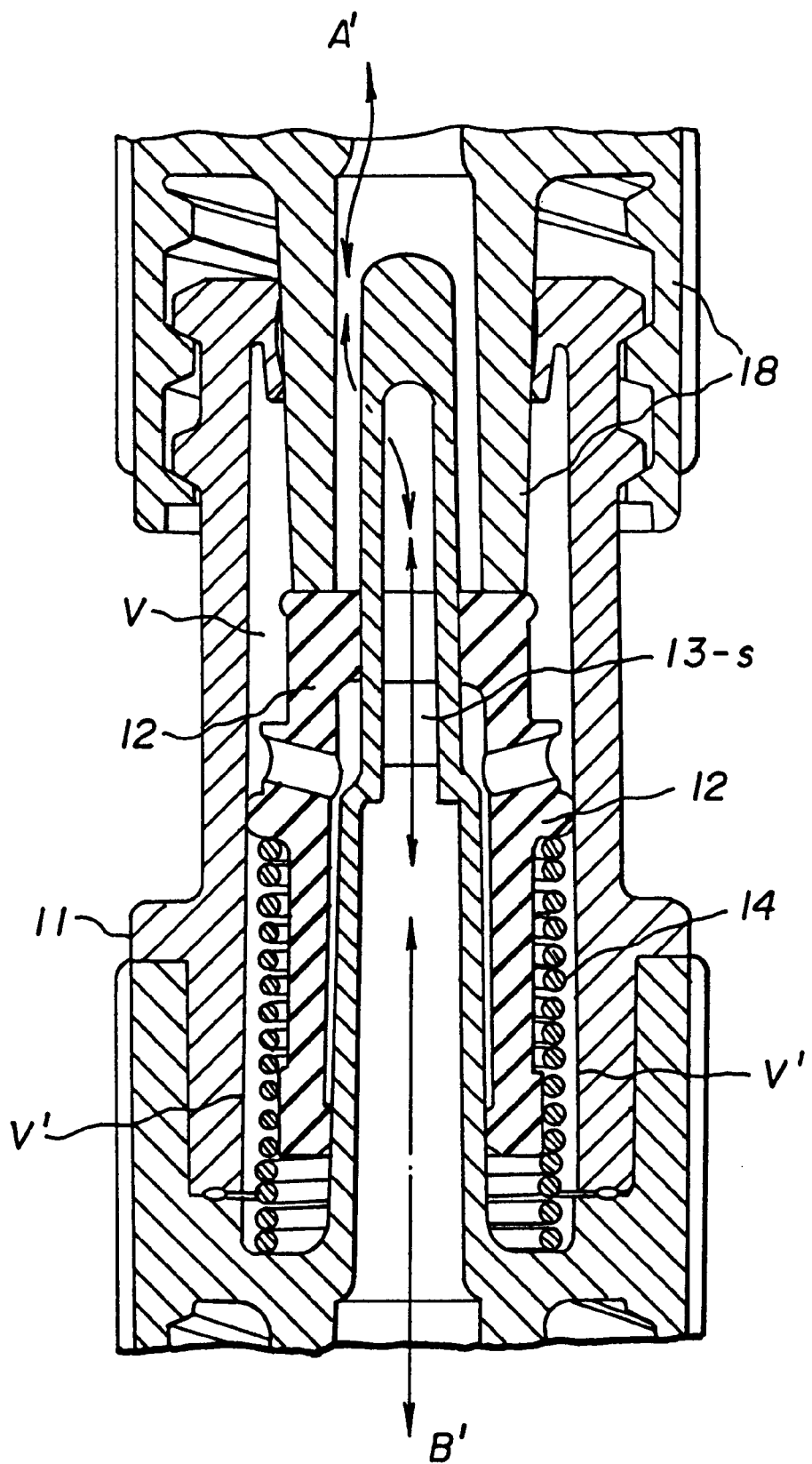
FIG. 1D is a sectional view showing the Luer tip of FIG. 1C further depressed to allow the passage of fluid from the Luer actuator through the check valve.
Figure 1E:
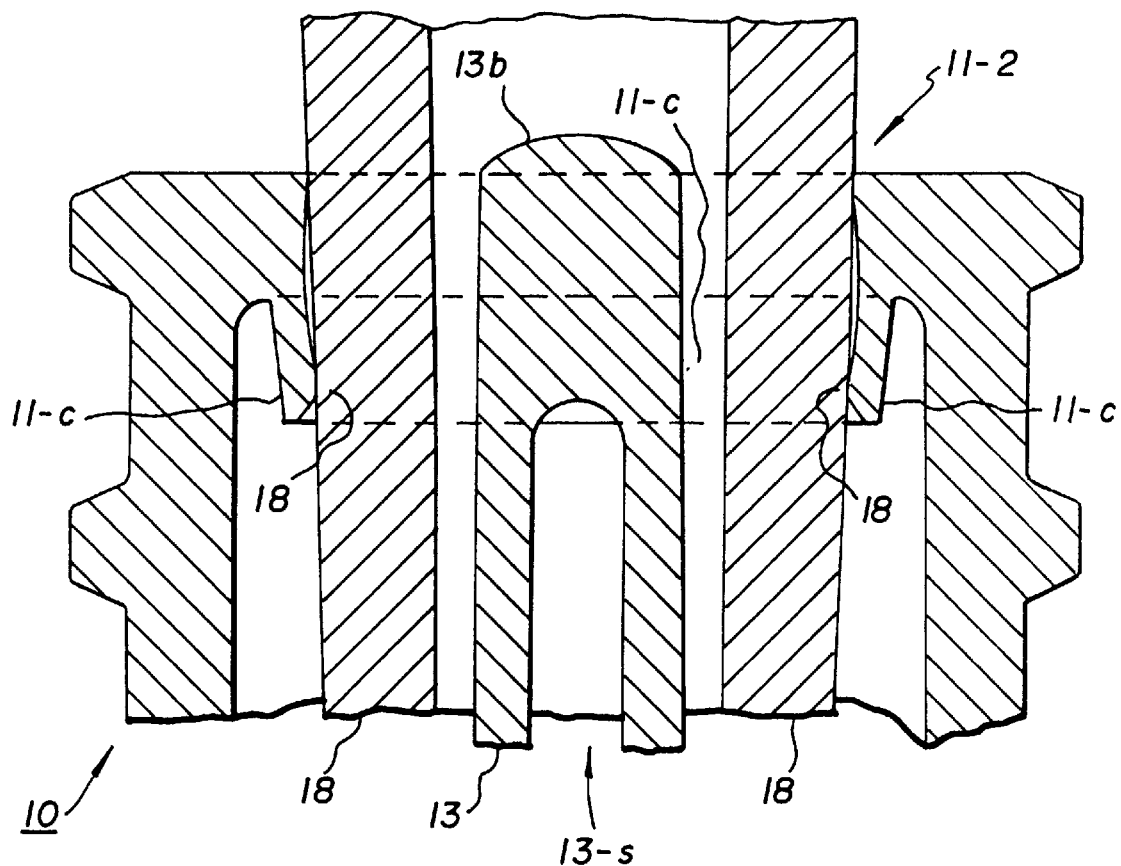
FIG. 1E is a partial enlarged sectional view of Fig. 1D showing the circular flexible seal of the invention that prevents reflux and accommodates a wide variety of Luer fitments and syringes.

Details of the circular flexible seal 11-c are shown in the enlarged cross section of FIG. 1E which indicates by the contact of the seal 11-c with the probe 18 how back pressure against the seal 11-c ensures closure of the inlet to prevent any flow out of the inlet. In addition, the flexibility of the walls for the seal 11-c allow the valve 10 to accommodate a wide variety of Luer fitments and syringes since the inlet 11-i can have a diameter that will receive the largest diameter fitment while the seal 11-c assures closure around the smallets diameter fitment below the inlet.

The nature of the through-passage is illustrated by FIGS. 1B and 1D. In Fig. 1D the flow is confined to the slot 13-s and there is flow into the interval V between the seal 12-s and the housing 11. The flow is confined to the bore B', with no flow in the interval V' between the spring 14 and the housing 11, a seal being provided by the spring 14 bearing against a support ring 12-s of the member 12, establishing a seal of the member 12.

Figure 2A:
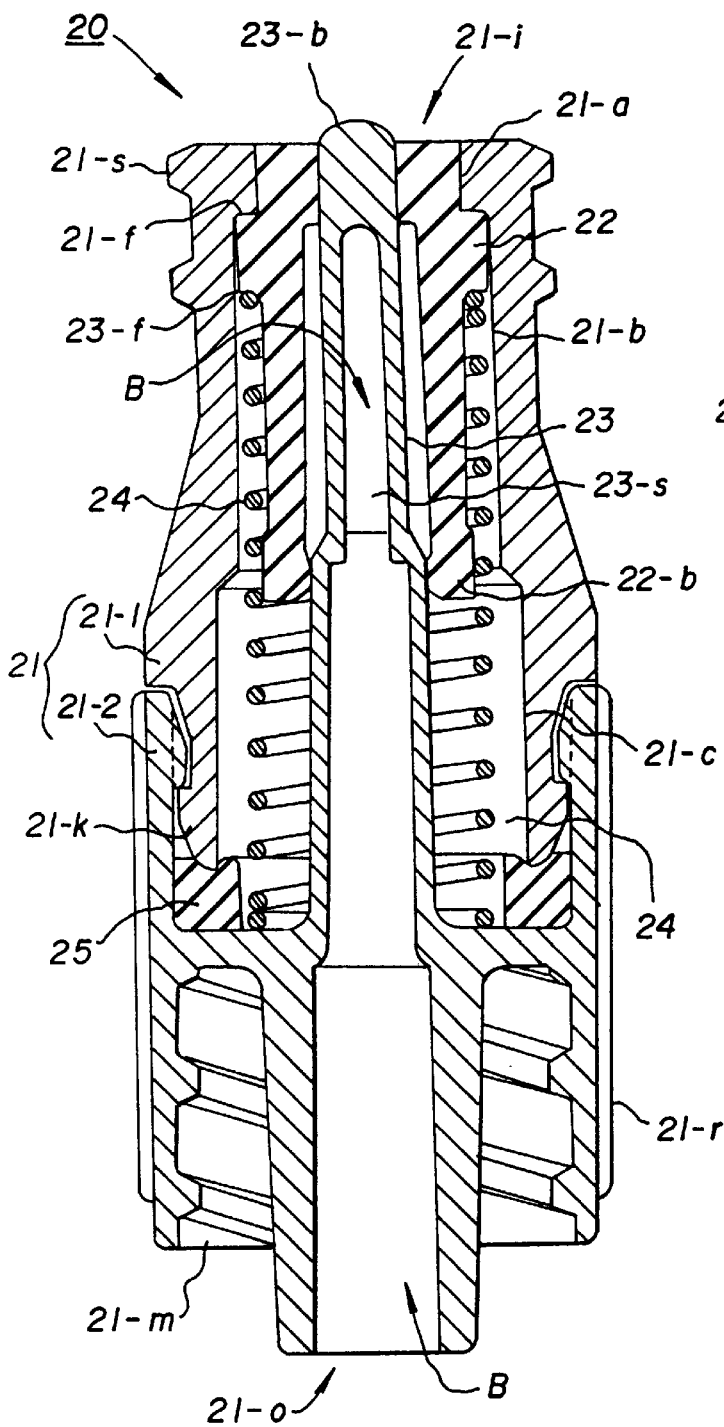
FIG. 2A is an enlarged section, taken along a diameter, through a swabbable check valve embodying the invention.

With further reference to the drawings, the check valve 20 of FIG. 2A includes a tubular housing 21 with two parts 21-1 and 21-2. The part 21-1, which occupies an "upper" position in FIG. 2A, contains an annular sealing member 22 that surrounds the upper portion of a stationary probe 23. The probe 23 is centered in the bore B of the housing 21 and contains an axial slot 23-s that extends to bore B of the housing 21.

The upper portion of the sealing member 22, below the inlet 21-i of the housing 21, slidably engages the upper end of the probe 23, while the intermediate portion of the sealing member 22, adjoining the slot 23-s, is spaced from the probe 23, which is in sealing engagement at the base 22-b.

A closed and blunt end 23-b of the probe 23 is elevated above the valve inlet 21-i to serve as a locator for an external member by which the sealing member 22 is depressible, as explained below. The sealing member 22 is held in its operative sealing position against a bore flange 21-f by a helical spring 24 acting against a flange 23-f of the sealing member 23.

The parts 21-1 and 21-2 of tubular housing 21 are joined together by a snap lock 21-k, with the upper part 21-1 in contact with a circumferential seal 25 that is supported by the lower part 21-2. The bore B of the housing upper part 21-1 has portions 21a, 21b and 21c, of different diameters. The bore portion 21a serves as a female Luer inlet and has its walls tapered accordingly. The portion 21-b is enlarged to accommodate the main body of the sealing member 22 and sliding seal 22-s. The seal plug 22 is surrounded by the spring 24 and thus supports the seal 22-b, while the portion 21c accommodates the compression of the spring 24.

Figure 2B:
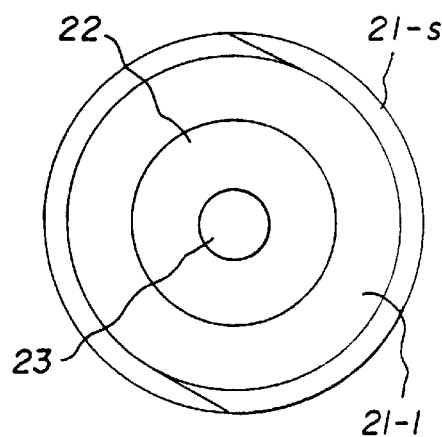
FIG. 2B is a top view of the swabbable check valve of FIG. 2A before sectioning.

The exterior of the housing 21 is provided at its inlet end 21-i, also shown in FIG. 2B, with threads 21-t and has a a male Luer 21-m at its outlet end 21-o. The portion 21-2 has ribs 21-r. The functions of the threads 21-t and the male Luer 21-m will presently become apparent. The housing may be formed of any suitable material, such as an elastomer or synthetic resin capable of being formed or molded.

Figure 2C:
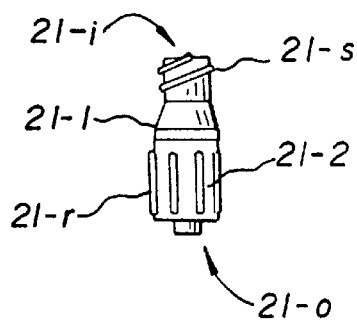
FIG. 2C is a full-scale view of the swabbable check valve of FIG. 2A, with its top view shown in FIG. 2D.
Figure 2D:
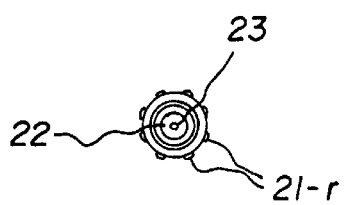

While the valve 20 of FIG. 2A has been shown enlarged for clarity, the invention contemplates miniaturization as indicated by the full-scale elevational view of FIG. 2C and the corresponding top view of FIG. 2D.

The annular sealing member 25 is an elastomeric ring having an outer diameter slightly larger than the inner diameter of the lower part 21-2, and encircles the lower portion of the spring 24. The probe 23 is hollow, desirably of the same material as the housing, and closed at its outer end 23-b, capping a hollow interior that extends outwardly to the outlet 21-o and communicates, in the upper part of the probe 23, with region between the probe and the member 22 by way of the slot 23-s.

While the sealing member 22, desirably elastomeric, is shown as being of a length shorter than the axial dimension of the housing 21, it may be elongated and incorporated functionally into the spring 24, which surrounds the co-axially mounted probe 23. The probe 23 is fixedly held, preferably by being integral with, and extending upwardly from the lower part 21-2. Like the tubular housing 21, the probe 23 can be formed of a moldable plastic, such as nylon.

Figure 3B:
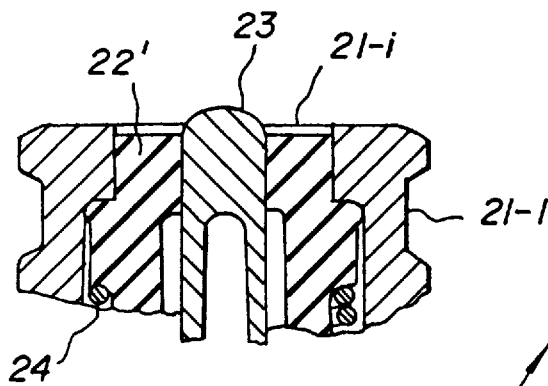
FIG. 3B is an alternative embodiment with a modified upper portion for the swabbable check valve of FIG. 2A.
Figure 3A:
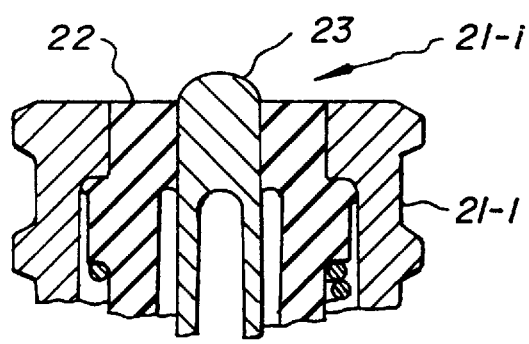
FIG. 3A is a partial view of the upper portion of the swabbable check valve of FIG. 2A.
Figure 3C:
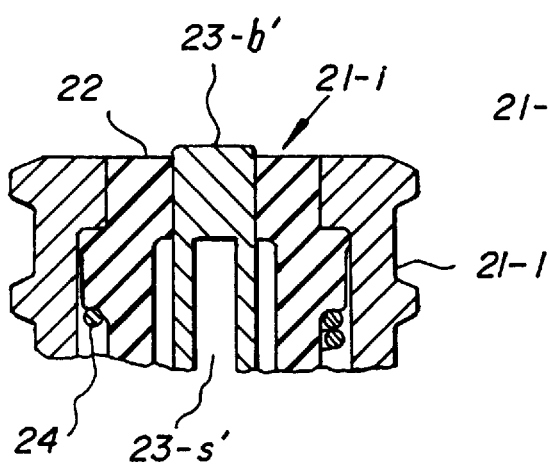
FIG. 3C is another alternative embodiment with a modified upper portion swabbable check valve of FIG. 2A.

Since the valve 20 is operated by an external member such as the Luer end of a syringe, the tip 23-b of FIG. 2A, which has been reproduced in FIG. 3A, serves as a fitment locator, of which FIG. 3A is merely representative. Although the outer end of the sealing member 22 is flush with the inlet 21-i in FIG. 3A, it may be depressed as shown for the member 22' in FIG. 3B, and the tip 23-b may be squared as illustrated by the tip 23-b' of FIG. 3C.

Figure 4A:
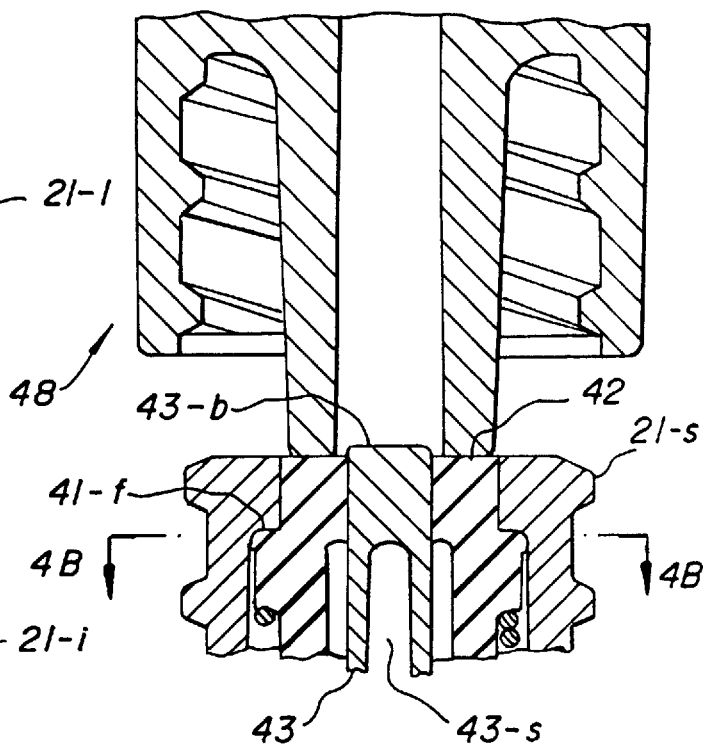
FIG. 4A shows the swabbable check valve of FIG. 3C being engaged by the Luer end of a syringe preparatory to needleless injection of fluid through the valve.
Figure 4B:
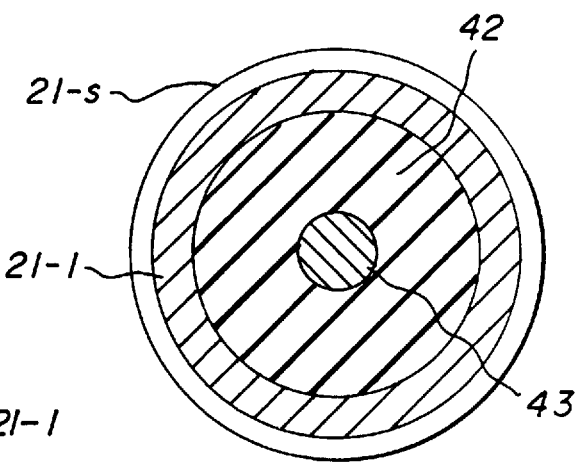
FIG. 4B is a sectional view of FIG. 4A, taken along the lines 4B—4B, illustrating the sealing of the inlet.

When the valve 20 is to be operated, an external member such as the male Luer outlet 48 of FIG. 4A is brought into contact with the sealing member 42, after being guided in position by the locator tip 43-b of the probe 43. It will be noted that the outlet 48 corresponds to the outlet 21-m of FIG. 2A and can take the form of the tip of a syringe. From an inspection of the cross-section shown in FIG. 4B, it will be apparent that the sealing member 42 provides a fluid-tight fit with the shoulder 41-f and with the outer unslotted end portion of the probe 43.

It also is evident that the sealing member 42 may be pushed or forced inwardly from its normal seating position. When forced inwardly as shown in FIG. 4C, the sealing member 42 extends below the transverse slot 43-s and thus establishes open communication for fluid through the housing 41 in either direction, e.g. inwardly or outwardly of the valve 40, as indicated by the double-headed arrows A.

The nature of the through-passage is illustrated by FIGS. 4D and 4E. In FIG. 4D the flow is confined to the slot 43-s and there is no flow in the interval I between the sealing member 42 and the housing 41. In FIG. 4E the flow is confined to the bore B, with no flow in the interval I' between the spring 44 and the housing 41, but with a seal being provided by the spring 44 bearing against a support ring 42-s of the member 42, establishing a seal of the member 42 against the probe 43.

The check valves 20 and 40 of the invention have a wide variety of uses, besides with catheters and the like. One such use is illustrated in cross-section in FIG. 5 where a valve substantially like the valve 20 of FIG. 2A has been incorporated into a "Y" site 50, that can be used, for example, in an IV (IntraVenous) procedure where the inlet branch IB of the Y site is connected to a container of solution that is fed through an outlet branch OB to a patient. The side branch SB of the site 50 can be used to inject medication into the patient. In prior practice the side branch SB channel C would be accessed through a needle actuated valve, but in the interest of avoiding needle sticks, needleless valves have been substituted. However, as noted above, the typical needleless valve has a long inlet channel in which contaminants and pathogens can accumulate.

Figure 5:
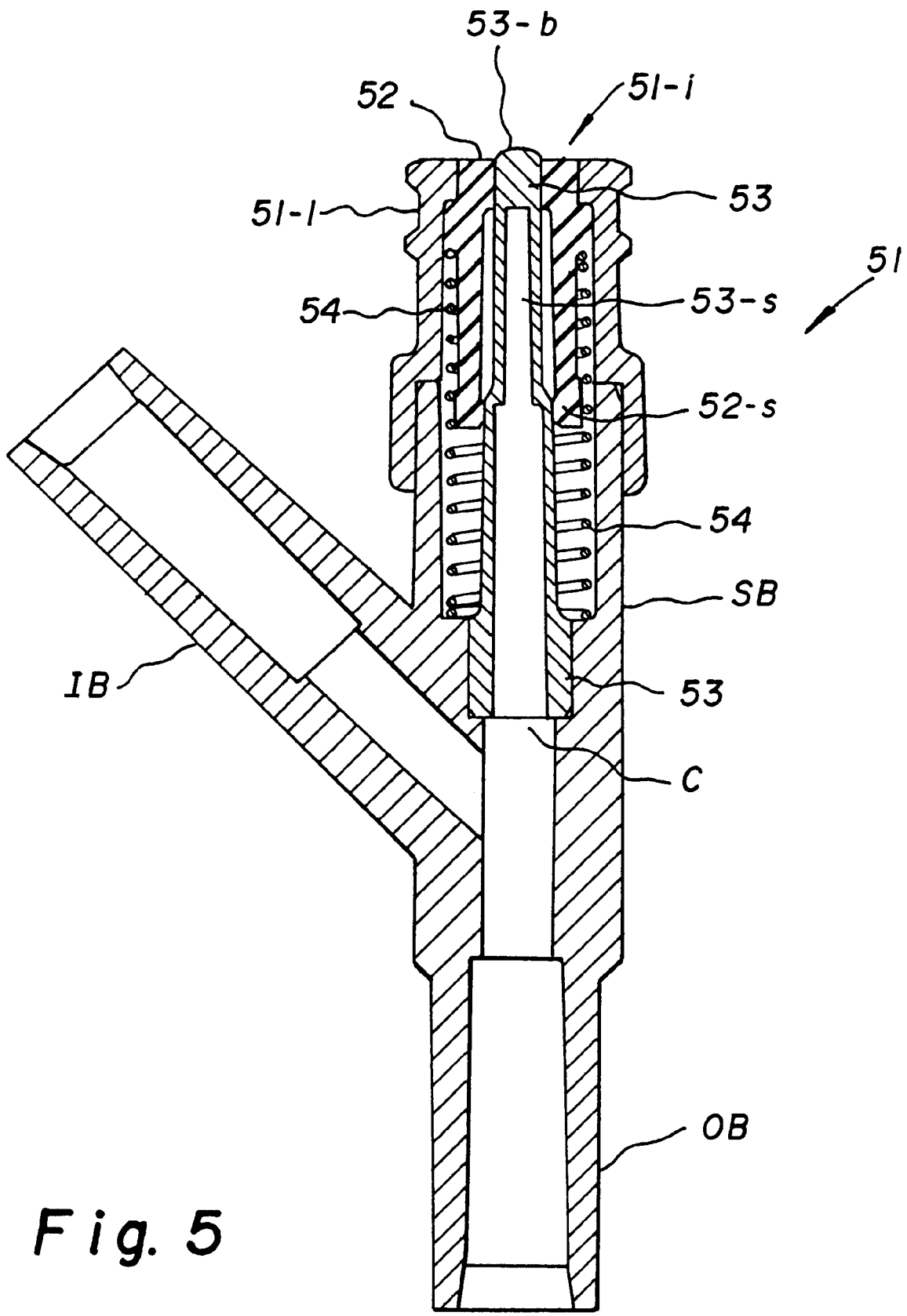
FIG. 5 is a sectional view of a "Y" site incorporating the swabbable check valve of the invention.

When the valves of the invention are adapted to form the valve 51 of FIG. 5, the inlet 51-1 is swabbable by being wiped with a disinfectant so that when a Luer fitting is brought into contact with the sealing member 52, after being guided by the fitment 53-b, the desired medicament can be infused with reduced chance of contamination and no need to used a needle mounted syringe to make the injection. Parts 51-1, 52, 52-s, 53, 53-s and 54 correspond to the parts 21-1, 22, 22-s, 23, 23-s and 24 of FIG. 2A.

Figure 6A:
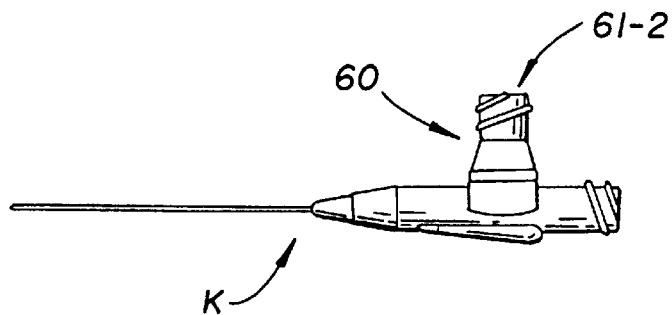
FIG. 6A is a plan view of a check valve with reflux protection adapted for use with a catheter.

The check valve 10 of the invention has a wide variety of uses. One such use is illustrated in FIG. 6A where a further valve 60 of the invention has been incorporated into a catheter K, that can be used, for example, in an IV (Intravenous) procedure. In prior practice the catheter K would be accessed through a needle actuated valve, but in the interest of avoiding needle sticks, needleless valves have been substituted. However, as noted above, the typical needleless valve has a long inlet channel in which contaminants and pathogens can accumulate.

When the valve 10 of the invention is adapted to form the valve 60 of FIG. 6A, the inlet 61-1 is swabbable by being wiped with a disinfectant so that when a Luer fitting is brought into contact with the sealing member 62, after being guided by the fitment 63-b, the desired medicament can be infused with reduced chance of contamination and no need to used a needle mounted syringe to make the injection.

As shown in FIGS. 6B through 8B, parts 61-1, 62, 62-s, 63, 63-s and 64 correspond to the parts 11-1, 12, 12-s, 13, 13-s and 14 of FIG. 1A, with the exception that the part 62 has been modified to provide a circular flexible seal 62-c at the interior of the part 62 instead of being associated with the upper part 61-1 as shown in FIG. 1A. In addition, the slot 63-s of the probe 63 is positioned well below the tip 63-b so that fluid back pressure through the bore R enters a channel L between the probe 63 and the inner wall of the member 62, and is directed against the flexible circular seal 62-c.

Figure 6B:
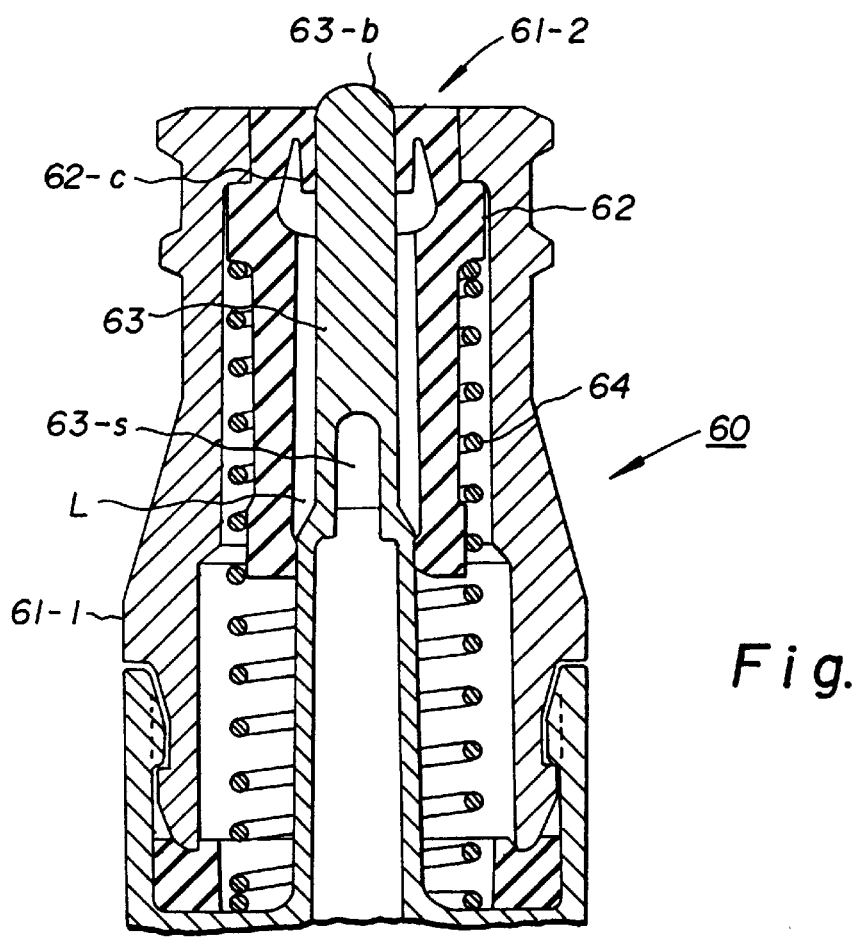
FIG. 6B is an enlarged cross-sectional view of the check valve of FIG. 6A taken along the lines 6B—6B shown in FIG. 6C.
Figure 6C:
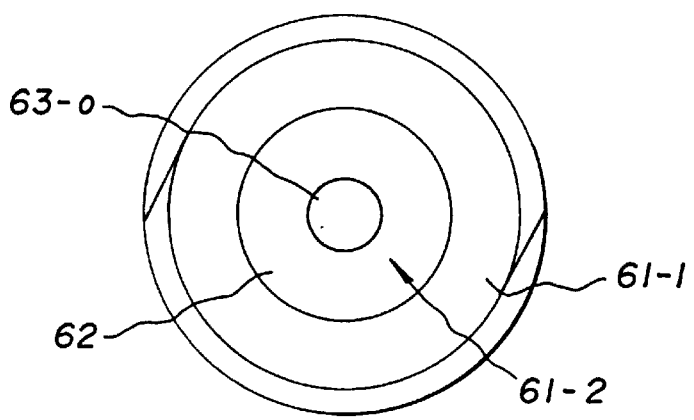
FIG. 6C is a top view of the check valve of FIG. 6B.
Figure 7A:
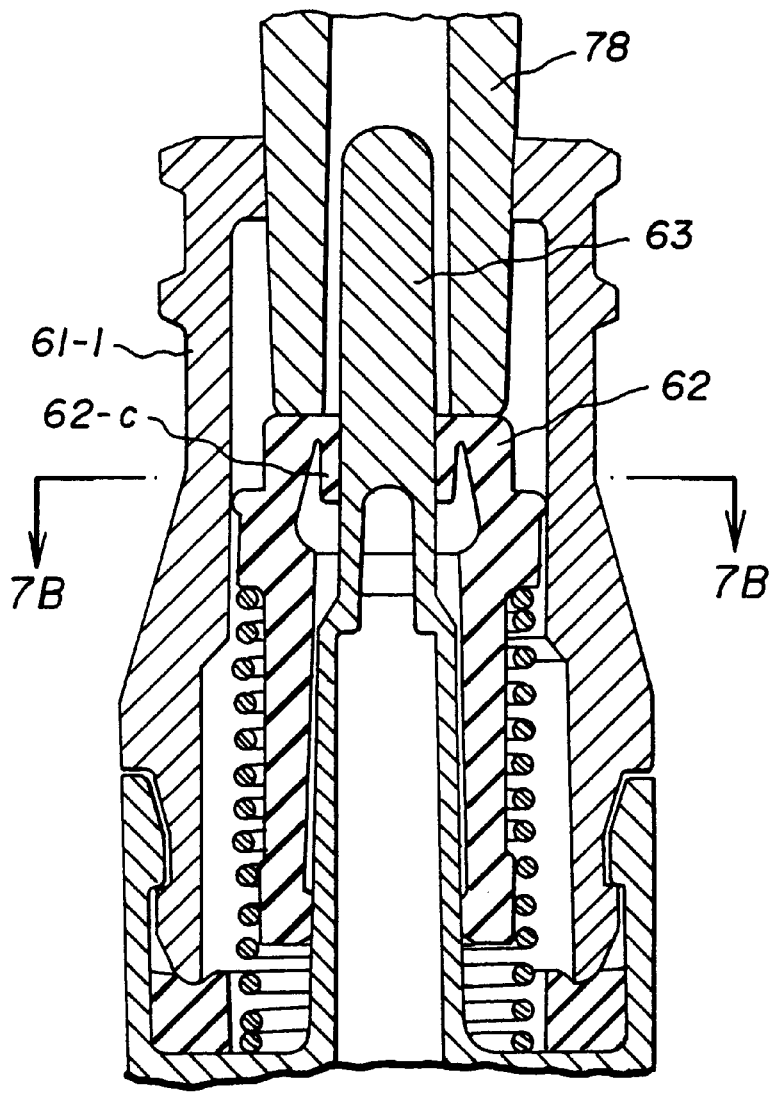
FIG. 7A shows the valve of FIG. 6B secured to a Luer actuator.
Figure 7B:
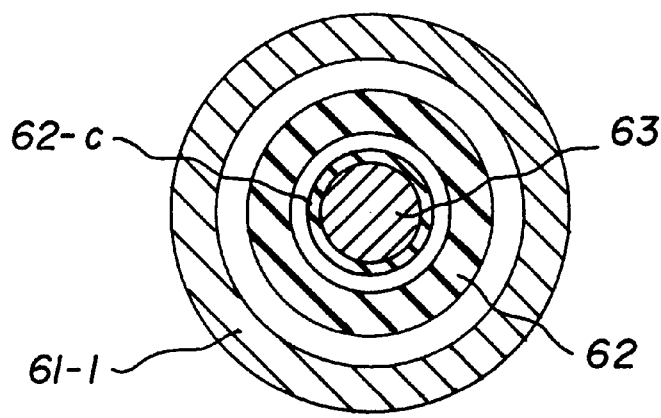
FIG. 7B is a cross-section of the valve of FIG. 7A taken along the lines 7B—7B.
Figure 8A:
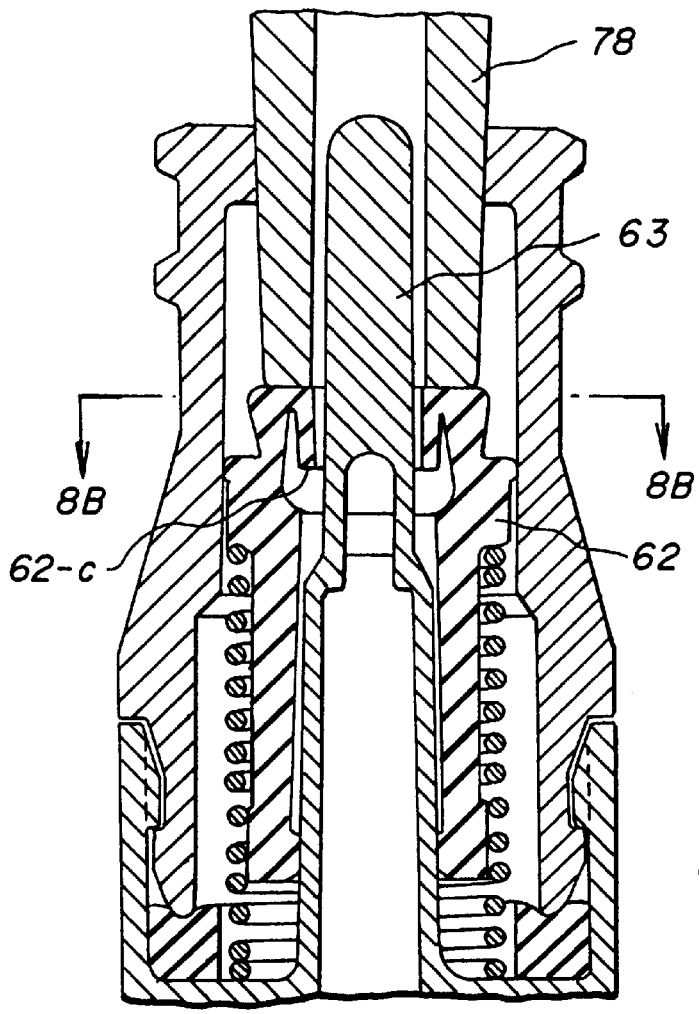
FIG. 8A is a cross-section of the valve of FIG. 7A showing activation of the valve by fluid pressure.
Figure 8B:
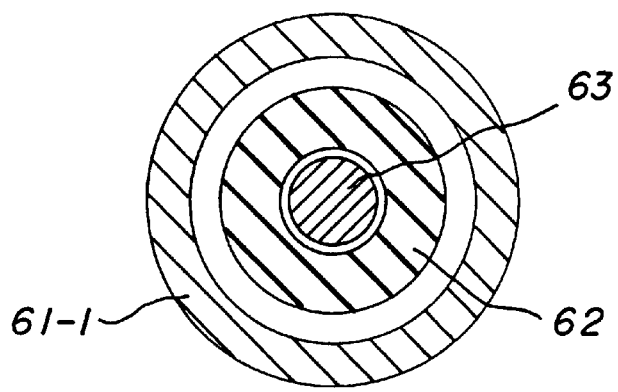
FIG. 8B is a cross-section of the valve of FIG. 8A taken along the lines 8B—8B.

Consequently, when the tip 78 of FIG. 7A is seated on the member 12, there is no flow through the tip 78. However, when fluid pressure is exerted through the tip 78 as shown in FIG. 8A, the flexible circular seal 62-c is moved away from the probe 63 to allow one-way fluid passage into the bore R and into the catheter of FIG. 6A. By contrast with the valve 10 of FIG. 1A, the valve 60 of FIGS. 6A and 6B is pressure-activated by fluid pressure through the Luer tip 78.

While preferred embodiments have been shown and described, it is to be understood that changes in details of construction and method from what has been illustrated may be made without departing from the spirit and scope of the invention as defined by the appended claims.

What is claimed:

1. Apparatus comprising
a housing having an inlet and an outlet
an inwardly biased flexible seal depending from said inlet to engage and seal a fitting as it enters said inlet;
a stationary probe within said housing extending axially from said outlet to said inlet;
said probe having a passageway thereinto connected to said outlet; and
means surrounding said probe and connected to said flexible seal for sealing said input when there is a reflux said of fluid into said outlet.

2. Apparatus as defined in claim 1 wherein said flexible seal comprises a flexible circular seal having a wall extending downwardly and openly into the interior of said housing.

3. Apparatus as defined in claim 2 wherein said wall engages said means for sealing said input.

4. Apparatus as defined in claim 3 wherein said wall is included in a housing that surrounds said probe below said input.

5. Apparatus as defined in claim 4 wherein said probe includes a channel that permits flow from said output to said axially extending wall.

6. Apparatus as defined in claim 5 wherein said channel extends transversely in relation to said axially extending wall.

7. Apparatus as defined in claim 2 wherein said wall is the frustum of a hollow cone.

8. Apparatus as defined in claim 1 wherein an actuator is used to depress said means for sealing said input and pressure applied through said actuator opens a passageway to said outlet.

9. The method of limiting reflux flow in a valve formed by a housing having an input and an output comprising the steps of:

providing a stationary probe within said housing extending axially from said output to said input;

including in said probe a passageway thereinto connected to said output; and sealing said input in relation to said probe when there is a reflux of fluid into said output.

10. The method as defined in claim 9 further including the step of sealing said input by a flexible circular seal having an axially extending wall.

11. The method as defined in claim 10 further including the steps of surrounding said probe by a sealing member and engaging said member by said axially extending wall.

12. The method as defined in claim 11 further including the step of including said axially extending wall in a housing and surrounding said member below said input.

13. The method as defined in claim 12 further including the step of permitting flow from said output to said axially extending wall.

14. The method as defined in claim 13 including the step of providing a channel that extends transversely in relation to said axially extending wall to permit said flow.

15. The method as defined in claim 10 further including the step of axially extending said wall to form the frustum of a hollow cone.

16. The method as defined in claim 10 further including the step of engaging said probe by said axially extending wall.

17. The method as defined in claim 9 further including the step of applying an actuator to depress said sealing member and cause pressure applied through said actuator to open a passageway to said outlet.

18. A method of claim 9 further comprising the steps of:

engaging a circumferential input seal by a depressible member surrounding said probe and extending to said input; and depressing said member along said probe in sealing engagement therewith.

19. The method as defined in claim 18 further including the step of applying pressure at said input to unseal the engagement of said member with said probe.

* * * * *